United States Patent [19]
Whitaker et al.

[11] Patent Number: 5,998,150
[45] Date of Patent: *Dec. 7, 1999

[54] METHODS OF MEASURING URINARY MYELIN BASIC PROTEIN-LIKE MATERIAL

[75] Inventors: John Nicholas Whitaker; Robert David Kachelhofer; Beverly Ann Layton; Edwin Luther Bradley, Jr., all of Birmingham, Ala.; Sheila Loughran Burgard, Lake Bluff; Anthony Thomas Reder, Oak Park, both of Ill.; Wendy Jean Morrison, Vancouver, Canada; Guojun Zhao, Vancouver, Canada; Donald Winston Paty, Vancouver, Canada

[73] Assignee: UAB Research Foundation, Birmingham, Ala.

[*] Notice: This patent issued on a continued prosecution application filed under 37 CFR 1.53(d), and is subject to the twenty year patent term provisions of 35 U.S.C. 154(a)(2).

[21] Appl. No.: 08/723,581

[22] Filed: Oct. 1, 1996

Related U.S. Application Data

[63] Continuation of application No. 08/723,581, Oct. 1, 1996, abandoned
[60] Provisional application No. 60/004,659, Oct. 2, 1995.
[51] Int. Cl.[6] .................... G01N 33/53; G01N 33/566; G01N 33/567; G01N 33/536
[52] U.S. Cl. ................ 435/7.1; 435/7.1; 436/501; 436/504; 436/536; 436/540; 436/542; 436/804; 436/811
[58] Field of Search .................. 435/7.1; 436/501, 436/504, 536, 540, 542, 804, 811

[56] References Cited

U.S. PATENT DOCUMENTS 5,464,777   11/1995   Yip ................................ 436/98

OTHER PUBLICATIONS

Tietz, Norbert W. (ed.), Textbook of Clinical Chemistry, W.B. Saunders Company, Philadelphia, pp. 224–226 and 488–489, 1986.
Barry et al., "Myelin Basic Protein Peptides in Urine," Annals of Neurology, 31(3):345–346, Mar. 1992.
Baumhefner et al., "M120. Multiple Sclerosis: Effect of Clinical Disease Activity and Interferon Beta 1–b Treatment on . . . Urinary Myelin Basic Protein–Like Material," Ann. of Neurology, 38(2):315, Aug. 1995.
Deibler et al., "A Reinvestigation of the Amino Acid Sequences of Bovine, Rabbit, Monkey, and Human Myelin Basic Proteins," J. of Biol. Chem. 260(1): 472–474, Jan. 1985.
Gibson et al, "Amino Acid Sequence of Human Myelin Basic Protein Peptide 45–89 As Determined by Mass Spectrometry," J. of Biol. Chem.; 259(8):5028–5031, Apr. 1984.
Giovannoni et al., "Urinary Myelin Basic Protein–like Material as a Correlate of the Progression of Multiple Sclerosis," Ann. of Neurol, 40(1): 128–129, Jul. 1996.
Whitaker et al., "P107. Further Investigation of Urinary Myelin Basic Protein–like Material in Pateints with Multiple Sclerosis," Ann. of Neurol. 26(1): 149–150, Jul. 1989.
Whitaker, "Reply", Ann. of Neurol., 31(3) 346–348, Mar. 1992.
Whitaker et al., "Correlation of Clinical Features and Finding on Cranial Magnetic Resonance Imaging with Urinary Myelin Basic Protein–like Material . . . ", Ann. of Neurol., 35(5): 577–585, May 1994.
Whitaker et al., "Urinary Myelin Basic Protein–like Material as a Correlate of the Progressive Phase of Multiple Sclerosis," Ann. of Neurol. 36(2): 259–260, Aug. 1994.
Whitaker et al., "Reply", Ann. of Neurol., 40(1): 129, Jul. 1996.

*Primary Examiner*—Nita Minnifield
*Assistant Examiner*—Padma Baskar
*Attorney, Agent, or Firm*—Benjamin Aaron Adler

[57] ABSTRACT

The present invention provides a method of determining the status of a multiple sclerosis patient, i.e., predicting the transition from a status of relapsing-remitting to a progressive phase of multiple sclerosis, comprising the step of measuring the levels of urinary myelin basic protein-like material in the patient. The present invention also provides a method of determining the amount of lesions and total lesion area of a multiple sclerosis patient, comprising the step of measuring the levels of urinary myelin basic protein-like material in the patient. Further provided is a method of monitoring myelination in a developing child, comprising the step of: measuring the levels of myelin basic protein-like material in the urine of said child.

11 Claims, No Drawings

METHODS OF MEASURING URINARY MYELIN BASIC PROTEIN-LIKE MATERIAL

CROSS REFERENCE TO RELATED APPLICATION

This application is a continuing application of application U.S. Ser. No. 60/004,659, filed Oct. 2, 1995, now abandoned.

This is a continued prosecution application of Ser. No. 08/723,581 filed on Oct. 1, 1996, now abandoned.

BACKGROUND OF THE INVENTION

1. Field of the Invention

The present invention relates generally to the field of neurology. More specifically, the present invention relates to an assay measuring urinary myelin basic protein like material as a correlate of multiple sclerosis status.

2. Description of the Related Art

Multiple sclerosis (MS), an inflammatory, primary demyelinating disease of the central nervous system (CNS) affecting an estimated 350,000 persons in the United States (1), is typified by a chronic and unpredictable course. This variable course and the associated heterogeneity of disease renders clinical trials involving large groups and clinical management of the individual patient problematic. Based on disease course, multiple sclerosis patients are usually categorized (2, 3) as relapsing-remitting (RR), relapsing progressive, primary chronic progressive (CP) and secondary chronic progressive according to the clinical appearance and persistence of neurological deficit. The development of disease progression, whether from onset as in primary chronic progressive-multiple sclerosis or as secondary chronic progressive-multiple sclerosis subsequent to an earlier period of relapses, can be viewed as the failure of remission. The failure of remission, or progression, is the principal cause of disability and decline in the quality of life.

The natural history of multiple sclerosis has been studied extensively for clinical features or laboratory measurements which might predict, anticipate or parallel the future course of disease. Clinical characteristics which appear to predict a future progressive course include: (1) male gender; (2) later age of onset of the disease; (3) corticospinal and cerebellar involvement; (4) increased number of relapses in the first five years; and (5) shorter interval between the first and second relapse (2–4). The clinical scales for assessing progression of disability have certain limitations (5) but, in general, the functional status in a population of multiple sclerosis patients is better than usually envisioned (6), and patients, even with chronic progressive disease may go through periods of spontaneous stability (7). This imprecision in clinical patterns and natural history requires clinical markers for signaling progression (8).

Several laboratory methods, including HLA typing (9) and cerebrospinal fluid (CSF) levels of tumor necrosis factors (10) have been reported to predict or parallel subsequent disease course in multiple sclerosis. Confirmation of these reported relationships have either not been successful (11) or conflicting (reviewed in 2). Serial cranial MRI, without or with gadolinium, represents another measure of clinical disease activity in multiple sclerosis (5, 12). Cranial MRI may predict the development of multiple sclerosis after initial signs (13), serve as a presumed surrogate marker in early multiple sclerosis (14) and demonstrate increasing lesion burden with longer duration of disease (12). The cranial MRI findings which are indicative of a chronic progressive course or which mark the transition from relapsing-remitting to chronic progressive disease are uncertain (15). Newer MRI techniques, such as magnetization transfer (16), may more accurately demonstrate the changes of chronic progressive-multiple sclerosis. Whatever the technique, cranial MRI may furnish an incomplete record about the change to a chronic progressive course which often results from involvement of the spinal cord.

Myelin basic protein (MBP), a protein of 170 amino acid residues, comprises 30% of CNS myelin proteins (17). Material, designated as myelin basic protein-like material (MBPLM), i.e., reactive with antibodies to myelin basic protein, normally exists at very low levels in CSF but increases after acute CNS myelin damage (18, 19). Serial sampling of CSF is not feasible, but the level of CSF myelin basic protein-like material in an multiple sclerosis patient with recent clinical worsening is predictive of a beneficial response to a regimen of intravenous methylprednisolone and oral prednisone (20). CSF myelin basic protein-like material has a molecular weight of >30,000 and appears to be bound to a carrier molecule (21). Myelin basic protein-like material in CSF is best recognized by an antibody reactive with an epitope that is represented in myelin basic protein residues 80–89 in a conformation present in the intact myelin basic protein molecule.

Urinary myelin basic protein-like material, usually found in low levels in normal individuals, is present in elevated levels in certain multiple sclerosis patients and is quite different in size and immunochemical features from the myelin basic protein-like material present in CSF (22). It has a molecular weight of <1000, is not bound to any other substances and appears to be similar to myelin basic protein residues 83–89 (22, 23). The level of urinary myelin basic protein-like material, unlike the level of myelin basic protein-like material in CSF, does not reflect acute disease activity in multiple sclerosis and correlates best with the existence of chronic progressive disease (23).

IFNβ-1b is the first therapeutic agent which can alter the natural history of relapsing-remitting-multiple sclerosis by reducing the number and severity of relapses and the volume of white matter involvement detected by cranial MRI (24). Although disease progression was not an end point in that trial of IFNβ-1b, there was a nonsignificant trend toward an effect of treatment on disease progression (24).

The prior art is deficient in the lack of effective means of determining the failure of remission or the presence of a progressive phase in patients having multiple sclerosis. The present invention fulfills this longstanding need and desire in the art.

SUMMARY OF THE INVENTION

In the multicenter, randomized placebo-controlled trial of alternate-day injections of recombinant interferon beta-1b (IFNβ-1b) in relapsing-remitting (RR) multiple sclerosis, urine specimens were collected periodically from all patients (n=64) in two of the clinical test sites over the two years of the study. Urines were also collected over two consecutive 24-hour periods from 43 patients from a third center. Urine samples were assayed for their content of myelin basic protein-like material, the level of which was correlated with a variety of clinical changes, cranial MRI results and the development of progressive disease. Concordant changes in creatinine values affected some of the relationships of myelin basic protein-like material. The level of urinary myelin basic protein-like material correlated with a chronic progressive (CP) course and with the number of lesions and the total lesion area on cranial MRI. A rise in the level of urinary myelin basic protein-like material antedates the clinical transition from a relapsing-remitting to a chronic progressive course. The randomized entry of patients led to significant differences in urinary myelin basic protein-like material among the three treatment groups, thus precluding correlation studies of treatment effects. However, the patient group from which 24-hour specimens were collected showed that the relapsing-remitting-multiple sclerosis patients changing to a chronic progressive course, and more specifically, those chronic progressive patients receiving placebo, had the highest values of urinary myelin basic protein-like material. Thus, the present invention demonstrates that urinary myelin basic protein-like material offers an objective test and can serve as a surrogate marker for detecting or predicting the failure of remission or the transition to a progressive phase of multiple sclerosis.

In one embodiment of the present invention, there is provided a method of determining the status of a multiple sclerosis patient, i.e., predicting the transition from a status of remission to a progressive phase of multiple sclerosis, comprising the step of measuring the levels of urinary myelin basic protein-like material in the patient.

In another embodiment of the present invention, there is provided a method of determining the amount of lesions and total lesion area of a multiple sclerosis patient, comprising the step of measuring the levels of urinary myelin basic protein-like material in the patient.

In another embodiment of the present invention, there is provided a method of monitoring myelination in a developing child, comprising the step of: measuring the levels of myelin basic protein-like material in the urine of said child.

Other and further aspects, features, and advantages of the present invention will be apparent from the following description of the presently preferred embodiments of the invention given for the purpose of disclosure.

DETAILED DESCRIPTION OF THE INVENTION

In the present invention, study of patients from three of the trial sites participating in the IFNβ-1b trial provides evidence that an elevated level of urinary myelin basic protein-like material correlates with or predicts the failure of remission or the presence of a progressive phase in multiple sclerosis. As such, it serves as a surrogate marker for the future clinical change in a patient. A person having ordinary skill in this art would readily recognize such changes in the clinical status of the multiple sclerosis patient and, inter alia, adjust the pharmacotherapy accordingly.

The present invention is directed to a method of determining the status of a multiple sclerosis patient by predicting the transition from a status of remission of multiple sclerosis to a status of a progressive phase of multiple sclerosis, comprising the step of: measuring the levels of myelin basic protein-like material in the urine of said patient. Preferably, the measuring is by a radioimmunoassay of myelin basic protein-like material, such as a double-antibody radioimmunoassay. More preferably, the double-antibody radioimmunoassay uses rabbit antiserum 110 (R110), radioiodinated myelin basic protein residues 45–89 as a radioligand and myelin basic protein residues 83–89 as an assay standard.

The present invention is also directed to a method of determining the amount of lesions and total lesion area of a multiple sclerosis patient, comprising the step of: measuring the levels of myelin basic protein-like material in the urine of said patient.

The present invention is further directed to a method of monitoring myelination in a developing child, comprising the step of: measuring the levels of myelin basic protein-like material in the urine of said child. Generally, this method would be useful in a child that suffers from a known a demyelinating condition in which the levels of myelin basic protein-like material in the urine of the child could be used to monitor the course of the demyelinating disease.

The following examples are given for the purpose of illustrating various embodiments of the invention and are not meant to limit the present invention in any fashion.

EXAMPLE 1

Patients and Treatment Groups

From the population of 372 multiple sclerosis patients, all relapsing-remitting (RR) at the beginning of the study, entered in the Betaseron® (Interferon beta-1b or IFNβ-1b) therapeutic trial (24), a total of 107 patients from three of the 11 study sites were included. The Institutional Review Boards at the three study sites approved the investigations conducted. The patient population consisted of 12 patients from the University of Alabama at Birmingham (UAB), 52 patients from the University of British Columbia (UBC) and 43 patients from the University of Chicago. The patients were randomly and equally divided among three treatment groups which received, respectively, placebo, 1.6 million IU (0.05 mg) of IFNβ-1b or 8 million IU (0.25 mg) subcutaneously on alternate days. At the time of each clinic visit, patients were examined and assigned a Kurtzke Expanded Disability Status Scale score (EDSS) (25) and a Scripps score (26). In addition to determining difference and percentage change in the EDSS and Scripps scores, the occurrence and timing of conversion from a relapsing-remitting to chronic progressive (chronic progressive) phase were noted. Progression was defined as a confirmed increase in EDSS of one point over baseline.

Urine was collected at entry and before randomization in the trial and then annually on all patients from UAB and UBC (Group 1). In addition the patients at UBC had urines collected at six week intervals (Group 2) on the same day on which they had a cranial MRI (12, 24). In the UBC cohort, nine of the 52 patients failed to have their initial urine specimens collected at the start of the clinical trial. Although the significance of the findings is not altered by inclusion or exclusion of these nine patients, the means, medians and statistical differences described are adjusted for the nine.

As part of a separate study at the University of Chicago of the effect of IFNβ-1b on the adrenal cortex and corticosteroid excretion (27), urine was collected over two consecutive 24-hour periods on 43 patients with relapsing-remitting-multiple sclerosis. The length of time in the therapeutic trial at the time of sample collection ranged from 210 to 810 days. One of the collections was for the "on" day following IFNβ-1b administration, and the other was for the "off" day of the alternate day treatment regimen (24). A total of 85 specimens were available, 43 patients from the "on" day and 42 of the same 43 patients from the "off" day. Urine volume was determined (judged to be complete and accurate in 74 of the 85 collections), and a 15 ml aliquot was stored at −20° C. Of the 43 patients, 30 patients remained relapsing-remitting, i.e., nonprogressive, and 13 patients became progressive or chronic progressive. For the patient group with accurate 24-hour collection volumes, 27 patients remained relapsing-remitting and 10 patients became chronic progressive.

EXAMPLE 2

Reagents

Trifluoroacetic acid, Sequenal grade, was purchased from Pierce Chemical (Rockford, Ill.). Acetonitrile, ultraviolet grade, was obtained from Burdick and Jackson Laboratories (Muskegon, Mich.). Organic-free water for high-performance liquid chromatography (HPLC) was prepared by ultraviolet irradiation of Milli-Q (Millipore-Continental Water Systems, Bedford, Mass.) water in a Model 816 HPLC Reservoir (Photronix, Medway, Mass.). CM SEPHADEX C-25 (crosslinked dextran) was purchased from Pharmacia Fine Chemicals (Piscataway, N.J.). Aprotinin (Trasylol) was purchased from Mobay Chemical (New York, N.Y.).

EXAMPLE 3

Preparation of MBP and MBP peptides

MBP was isolated from bovine brain by delipidation, acid extraction at pH 3, and carboxymethylcellulose chromatography at pH 10.6. Components one to four were pooled, subjected to limited digestion with pepsin, and chromatographed on carboxymethylcellulose in 0.2 M ammonium bicarbonate at pH 7.6. The fraction, previously designated as $P_1$, was isolated and shown to be a mixture (30:70 ratio) of bovine basic protein peptides 45–89, bovine MBP peptide 43–88.

EXAMPLE 4

Preparation of Immunogen

Eleven milligrams of the bovine MBP peptides in chromatograph fraction $P_1$ was combined with 11 mg of ovalbumin in 2.75 ml of distilled water and stirred at 25° C. Fourteen milligrams of 1-ethyl-3 (3-dimethyl-aminopropyl) carbodiimide hydrochloride was added and the stirring at 25° C. continued for 22 hours. The solution was then dialyzed at 4° C. against one liter of distilled water over 4 days; the dialysis bath was changed daily. The dialyzed material was then frozen and stored at −20° C.

EXAMPLE 5

Immunization Protocol

An emulsion was made by mixing 200 μl of the bovine MBP peptide-ovalbumin conjugate with 1.8 ml of 0.15 M NaCl and 2.0 ml of complete Freund's adjuvant supplemented with 10 mg of mycobacterium H37RA. This mixture was homogenized in Virtis 23 at high speed for 2 minutes at 25° C. The emulsion was used to immunize (R110 and R111) New Zealand white female rabbits weighing 2.5 kg. Each animal received 0.25 ml in each footpad and 0.5 ml intradermally in 12 sites on each flank for a total of 2 ml per animal. Assuming 100% efficiency in conjugation, each animal received 800 μg of peptide linked to ovalbumin. One month later each animal received the same amount of peptide-ovalbumin conjugate with the emulsion made with incomplete Freund's adjuvant and with no additional mycobacterium. The injections were made intramuscularly in each hind leg and subcutaneously over the shoulders and flanks. One week later the animals were bled. Four weeks after the boosting with immunogen-incomplete Freund's adjuvant, each animal received intraperitoneally 1 ml of 0.15 M NaCl to which had been added 20 μg of peptide-ovalbumin conjugate in an effort to prevent anaphylaxis. The next day each animal received intravenously 120 μg peptide-ovalbumin conjugate in 1 ml of 0.15 M NaCl. One week later the animals were bled on alternate days for a total of 100 ml in 3 bleedings. One month after the first intraperitoneal injection, the intraperitoneal and intravenous injections were repeated. The animals were bled twice during the following week, and one month later the intravenous injection was again repeated. The animals were bled the following week 3 times on alternate days for a total bleeding of 135 ml. This last bleeding, referred to as R110 GHI, is the serum used for the studies described herein.

EXAMPLE 6

Specimens

Urine was collected from an external or internal catheter or by voiding, as 24-hour or individual specimens, and was placed at 4° C. without preservative for up to 24 hours and then stored fresh at −20° C. Individual urine specimens were usually collected around 8:00 AM. In two men with chronic progressive MS whose urine was collected during 4-hour segments for 96 hours there was no consistent diurnal variation. Some urine samples were stored at −20° C. in the presence of 0.1% methylated bovine serum albumin (MBSA). Some samples of urine were dialyzed for 24 hours at 4° C. against distilled water. Dilutions of urine used for testing were made in dialyzed normal urine. Clinical conditions were designated independently of laboratory test. The diagnosis of MS was based on the Schumacher criteria. An exacerbation of MS was defined as the appearance of a new neurological deficit or the worsening of a previous one lasting 24 hours or longer and not explained by another cause.

Specimens of voided urine were obtained from 113 persons. These included 76 specimens from 26 normal control subjects, 59 specimens from 48 persons with other neurological diseases (OND), and 302 specimens from 39 persons with clinically definite MS. The OND group included a variety of neurological disorders including stroke within 10 days (8 patients), stroke one month or more previously (2 patients), neurodegenerative diseases (4 patients), sagittal sinus thrombosis (1 patient), and headache or functional disorders (4 patients).

EXAMPLE 7

Radioimmunoassay

A double antibody radioimmunoassay (DA-RIA) was performed at 4° C., with nonequilibrium conditions. Radioiodination was by lactoperoxidase-catalyzed iodination. The final volume of the DA-RIA was 950 μl. One day one, 450 μl of 0.2 M Tris-acetate buffer, pH 7.2 containing 0.2% (w/v) MBSA (TA-MBSA), was placed in 12×75 mm plastic tubes, and 200 μl of diluted first antibody was placed in a 1:200 dilution of normal rabbit serum in 0.2 M Tris-acetate buffer (A), pH 7.2. Two different primary antibodies were used, but otherwise the assays were identical. The first antibody, R110, was used at a final dilution of 1:8,550. R79 was used at a final dilution of 1:3,800. Fifty microliters of MBP or MBP peptide in TA-MBSA or 50 μl of CSF or urine was added. When less than 50 μl of body fluid was tested, it was mixed with enough TA-MBSA to give the sample a total volume of 50 μl. After 16 hours, 50 μl of TA-MBSA containing approximately 10,000 cpm of $^{125}$I-human MBP peptide 45–89 was added and allowed to stand for 20 hours. Two hundred microliters of goat antirabbit IgG, diluted 1:4 in TA, was added. After 20 hours, the pellets were collected, washed, and counted on a gamma counter. Results of DA-RIA were charted by a logit-log method. For calculations of molar inhibitions, each amino acid residue in the protein or peptide was assigned a molecular weight of 100.

EXAMPLE 8

Processing of Urine Specimens Before HPLC

Two milliliters of urine was centrifuged at 3,000 rpm to remove any particulate matter and adjusted to pH 5 with 1

M acetic acid and 0.1 M ammonium acetate, pH 5.0. This specimen was applied to a 0.7×2.5 cm column of CM SEPHADEX C-25 (crosslinked dextran) that had been equilibrated with 0.02 M ammonium acetate, pH 5.0, and washed with 5 ml of the same buffer, all at 25° C. The effluent (7 ml) was collected in one vial labeled "flow-through." Material that had bound to the column was eluted with 3.5 ml 1 M ammonium hydroxide. The eluate was collected in one vial and was immediately adjusted to pH 6 to 7 with 1 M acetic acid. A 4-ml portion of water was added to the eluate, and both flow-through and eluate were lyophilized twice. The residue was dissolved in 2 ml water. By DA-RIA only the flow-through was shown to contain the urinary MBP-like material, so it was studied further by HPLC. The flow-through was chromatographed on a reverse-phase HPLC column.

EXAMPLE 9
HPLC

HPLC was performed on a Waters (Millipore, Waters Products Division, Milford, Mass.) liquid chromatograph equipped with two Model 6000A pumps, Model 660 solvent programmer, Model U6K injector, Model 450 variable-wavelength detector, and a Series B-5000 Omniscribe strip chart recorder (Houston Instrument, Austin, Tex.). A Vydac 218TP54 reversed-phase column ($C_{18}$, 25 cm×4.6 mm internal diameter, 5-μm particles), obtained from the Separation Group, Hesperia, Calif., and a Waters guard column packed with Bondapak $C_{18}$/Corasil (Millipore) were used.

Solvent A was 0.1% (v/v) trifluoroacetic acid in water. Solvent B was 0.1% trifluoroacetic acid in a mixture of 9 parts acetonitrile to 1 part water. Solvents were prepared fresh daily and were filtered and degassed with nylon-66 membrane filters (0.45 μm pore size) purchased from Rainin Instrument, Woburn, Mass. The composition of the mobile phase was adjusted using the solvent programmer with pure Solvent A from the A pump and pure Solvent B from the B pump.

The quantitative microcomplement fixation test was used. Urine was separated on SEPHADEX G-25 (dextran crosslinked with epechlorohydrin) equilibrated with 0.2 M $NH_4HCO_3$ at 4° C. Three milliliters of urine was applied to a 1.5×90 cm column and 1 ml fractions were collected. Fractions from this were used for testing in the DA-RIA. Also, mixtures of the DA-RIA incubation and samples were chromatographed on SEPHADEX G-25 (dextran crosslinked with epechlorohydrin) in the presence or absence of urine containing MBP-like material. In those determinations, the radioactivity of the eluted fractions was determined by gamma counting. Creatinine content in urine was measured with a kit assay (Sigma Chemical, St. Louis, Mo.) according to the prescribed protocol. Statistical evaluation was by comparison of means from independent samples and populations with unequal variances.

EXAMPLE 10
Quantitation of Urinary myelin basic protein-like material

Urinary myelin basic protein-like material was quantitated with a double-antibody radioimmunoassay (RIA) using rabbit antiserum 110 (R110), radioiodinated myelin basic protein residues 45–89 as radioligand and myelin basic protein residues 83–89 as assay standard. The details and features of this radioimmunoassay are described above. The concentration of urinary myelin basic protein-like material was expressed as ng/ml and also as ng myelin basic protein-like material per mg creatinine (22). The concentration of urinary myelin basic protein-like material was also measured with two other radioimmunoassays in which either rabbit antiserum 3794 (R3794) or monoclonal antibody (mAb) F41 served as first antibody, human myelin basic protein residues 69–89 served as the radioligand and the standard was human myelin basic protein residues 80–89. The characterization of reagents R3794 and mAb F41 and their quantitation of urinary myelin basic protein-like material by radioimmunoassay have been described (23).

EXAMPLE 11
Cranial MRI

Cranial MRI without gadolinium enhancement was performed according to specific protocol, and T2-weighted images were analyzed for Groups 1 and 2 (12). Cranial MRI at UBC was performed with a 0.15 T instrument, and those at UAB with a 1.0 T instrument. All MRI interpretations and measurements were made at UBC. For the cranial MRIs performed at UAB and UBC the number of lesions identified, designated previously as regions of interest (12), total lesion area and percent interval change in lesion area were determined. At UBC for the six-week interval study, the number of new lesions, number of recurrent lesions, number of enlarging lesions, number of activity events and percent of active scans were determined (12, 24).

EXAMPLE 12
Data Analysis and Statistics

Analysis was performed on urine specimens from three patient groups. Group 1 (annual study) consisted of all annually collected specimens at UAB and UBC. Group 2 (six-week study) were the specimens collected at six-week intervals at UBC. Annual data on all patients were analyzed so that there were 168 urine specimens from individuals studied on the first visit (start of trial), second visit (one year after beginning) and third visit (two years after beginning), which were correlated with a total of 36 clinical and neuroimaging variables. For the study of the cohort from UBC (Group 2) on whom urine was collected at six-week intervals, analysis was performed separately. Group 3 included 42 patients who had two consecutive 24-hour urine collections.

Continuous variables, such as urinary myelin basic protein-like material and creatinine, were summarized as mean +SD, and analyzed by a two-way (disease groups and visit) analysis of variance (ANOVA) with time treated as a repeated measures factor (28). Comparisons between disease groups at each visit and averaged over visits used a two-tailed unpaired Student's t-test (29). Comparisons among treatment groups at each visit and averaged over visits used a one-way ANOVA (29). Multiple comparisons among pairs of means used the Fisher's protected least significant difference method (29). Associations between urinary myelin basic protein-like material values and MRI measurements were computed with Pearson's correlation coefficient (30). Comparisons of attribute data with disease groups or treatment groups used a Chi square test of proportions (31). The univariate associations of time until progression occurred with the clinical and neurological variables utilized the log rank statistic (32) and the joint associations used Cox's proportional hazards model (33). Two factor analysis of variance (34) was used to analyze the treatment and disease course simultaneously on the clinical and neurological variables. Covariance analysis was used to assess the effect of the length of time a subject was in the study on the results (34). When group standard deviations increased directly with the group means, data were subjected to logarithmic transformation and reanalyzed (28). Differences were declared statistically significant if $p<0.05$.

EXAMPLE 13

Two urine measurements expressed separately as myelin basic protein-like material (ng/ml) and creatinine (mg/ml) or as a combined value of myelin basic protein-like material/creatinine (ng/mg), to correct for variations in patient glomerular filtration function, were the bases for a variety of correlations attempted. The general approach to analyzing the data was to search first for correlations overall during the study and secondly for predictive or parallel value of the measurements made at the beginning or at specified intervals. Since the urine measurements in Groups 1–3 had been an add-on to the clinical trial, some of the correlations could be viewed in a cautious fashion only as trends.

For the correlations overall, Groups 1 and 2 showed many similarities. The level of urinary myelin basic protein-like material correlated with both the number of lesions and the total lesion area detected by cranial MRI (TABLE 1). The data presented in TABLE 1 is expressed as a Pearson correlation coefficient and range of p-value for the sample size. Specific p-values are presented in this section. There was no correlation with the percent activity or the presence of new lesions by cranial MRI (TABLE 1). These relations implied, as had the results of a previous cross-sectional study (23) that the level of urinary myelin basic protein-like material did not correlate with active disease.

Levels of myelin basic protein-like material showed irregular correlations with disability scores. For Group 1 the level of myelin basic protein-like material correlated (p=0.0322) with EDSS score. A concordant increase in creatinine resulted in no significance (p=0.6211) to the correlation of EDSS and myelin basic protein-like material/creatinine. In Group 2 there was significant correlation of myelin basic protein-like material, expressed either as a level or in relationship to creatinine, with EDSS score and a significant, indirect relationship with the Scripps score. When measurements overall or at selected times were analyzed, there were scattered correlations of urine values with the number of lesions, the total lesion area detected by cranial MRI and the EDSS score (TABLE 1).

TABLE 1

Correlations Of Urinary Myelin Basic Protein-Like Material Variables With MRI And Clinical Measures

| | MRI | | | | Clinical | | |
| --- | --- | --- | --- | --- | --- | --- | --- |
| | Percent Activity | New Lesions | Number of Lesions | Total Area | EDSS | Scripps | Change Prog. |
| Group 1 Overall (N = 168) | | | | | | | |
| Creatinine (mg/ml) | 0.128 | −0.009 | 0.182[a] | 0.230[c] | 0.201[b] | −0.210[a] | 0.172 |
| MBPLM (ng/ml) | 0.018 | −0.034 | 0.179[a] | 0.215[c] | 0.165[a] | −0.088 | 0.147 |
| MBPLM/Cr. (ng/mg) | −0.103 | −0.095 | 0.113 | 0.133 | 0.038 | −0.003 | 0.102 |
| Group 1 Visit 1 (N = 55) | | | | | | | |
| Creatinine (mg/ml) | 0.235 | 0.395[b] | 0.267 | 0.237 | 0.256 | −0.161 | 0.285 |
| MBPLM (ng/ml) | 0.059 | 0.262 | 0.244 | 0.250 | 0.212 | −0.201 | 0.210 |
| MBPLM/Cr. (ng/mg) | −0.077 | −0.063 | 0.093 | 0.163 | 0.107 | −0.160 | 0.070 |

The numbers are the Pearson correlation coefficients. Values with statistically significant differences are shown in bold type and the range of p-values referenced as [a]p-value < 0.05, [b]p-value < 0.01, [c]p-value < 0.005. More precise p-values are presented below.

TABLE 2

Correlations Of Urinary Myelin Basic Protein-Like Material Variables With MRI And Clinical Measures

| | MRI | | | | Clinical | | |
| --- | --- | --- | --- | --- | --- | --- | --- |
| | Percent Activity | New Lesions | Number of Lesions | Total Area | EDSS | Scripps | Change Prog. |
| Group 2 Overall (N = 802) | | | | | | | |
| Creatinine (mg/ml) | 0.160[c] | 0.030 | 0.273[c] | 0.249[c] | 0.040 | −0.101[a] | 0.216 |
| MBPLM (ng/ml) | 0.034 | −0.034 | 0.248[c] | 0.237[c] | 0.074[a] | −0.112[a] | 0.257 |
| MBPLM/Cr. (ng/mg) | −0.164[c] | −0.127[c] | 0.082[a] | 0.124[c] | 0.097[b] | −0.110[a] | 0.169 |
| Group 2 Visit 1 (N = 43) | | | | | | | |
| Creatinine (mg/ml) | 0.243 | 0.380[a] | 0.267 | 0.258 | 0.304[a] | −0.161 | 0.250 |
| MBPLM (ng/ml) | 0.095 | 0.258 | 0.244 | 0.368[a] | 0.377[a] | −0.201 | 0.172 |
| MBPLM/Cr. (ng/mg) | −0.062 | −0.058 | 0.093 | 0.238 | 0.205 | −0.160 | 0.074 |
| Group 2 Visit 2 (N = 39) | | | | | | | |
| Creatinine (mg/ml) | 0.049 | −0.119 | 0.368[a] | 0.384[a] | 0.098 | −0.326 | 0.456 |
| MBPLM (ng/ml) | 0.196 | −0.016 | 0.421[b] | 0.402[a] | 0.282 | −0.235 | 0.475 |
| MBPLM/Cr. (ng/mg) | 0.024 | 0.052 | 0.292 | 0.185 | 0.297 | −0.033 | 0.144 |

The numbers are the Pearson correlation coefficients. Values with statistically significant differences are shown in bold type and the range of p-values referenced as [a]p-value < 0.05, [b]p-value < 0.01, [c]p-value < 0.005. More precise p-values are presented below.

EXAMPLE 14
Urinary MBPLM and Change to Progressive Course

When analyzed for correlation of urinary myelin basic protein-like material with the change from relapsing-remitting to a chronic progressive course, there was a borderline correlation (p=0.0573) for Group 1 but a highly significant correlation (p=0.0001) for Group 2 (Table 2). These differences in level of significance may be due to differences in sample size. The confounding part of this analysis was the unexpected behavior of creatinine which was higher concordantly with myelin basic protein-like material. For Group 1, but not for Group 2, this paralleling change in creatinine abolished the statistical significance of the correlations of myelin basic protein-like material with changes on cranial MRI (Table 1). For Group 2, there was a significant correlation (p=0.02 or better) of the measurements of creatinine, myelin basic protein-like material or myelin basic protein-like material/creatinine with the number of lesions and total lesion area on MRI and with the change of relapsing-remitting to chronic progressive in disease course (TABLE 2). Consistent with the earlier report of no correlation between disease activity and urinary myelin basic protein-like material/creatinine (23), there was a significant negative correlation (p=0.0159), or indirect relationship, between the value of urinary myelin basic protein-like material/creatinine and the number of relapses.

The urinary level of myelin basic protein-like material was significantly higher in the relapsing-remitting-multiple sclerosis patients who had shifted to a chronic progressive course than those who had retained the relapsing-remitting pattern. This was especially noted in the Group 2 cohort of 52 patients who had urine specimens obtained every six weeks and, thus, a larger number of samples for analysis. Those who became chronic progressive had a value of urinary myelin basic protein-like material of $198.5\pm6 0$ ng/ml compared to a value of $129.0\pm81$ ng/ml in the relapsing-remitting patients (p=0.0042). The parallel change in creatinine had the effect of changing the relationship of myelin basic protein-like material/creatinine and transition of relapsing-remitting to chronic progressive-multiple sclerosis to only a trend (p=0.0752).

When the data from Group 2 were plotted over the course of the trial, the mean value of myelin basic protein-like material was always higher in the chronic progressive compared to the relapsing-remitting group, with this difference significant (p<0.05) by six weeks and for nine of the 18 intervals for urine specimen collection. The mean day of onset of the chronic progressive from the relapsing-remitting phase in Group 1 was 566 days. The median for this change was 394 days reflecting the long times in some patients for this change to occur. Specifically, of the 19 relapsing-remitting patients who became chronic progressive, nine did so within the first year, four did so between years one and two, three between years two and three, and three after the third year. When the combined data of Groups 1 and 2 were analyzed in regard to a temporal relationship of the urinary myelin basic protein-like material value and the transition of disease phases, a precise temporal relationship could not be determined, but it was evident that the urinary myelin basic protein-like material elevation must have antedated the transition in disease phases by months. Thus, before the transition, the mean value of the chronic progressive group (specimens N=150) was 199.9 ng/ml and 190.6 ng/ml afterwards (specimens N=93). In the relapsing-remitting group (specimens N=591) the mean value was 131.2 ng/ml.

Because of the impact of the elevated creatinine values, the availability of 24-hour urine collections from Group 3 presented an opportunity to address this question with more optimal urine measures. Subject means of urinary creatinine, myelin basic protein-like material (ng/ml or ng per 24 hours) or myelin basic protein-like material/creatinine values showed no significant differences in regard to the "on" or "off" day of administration of IFNβ-1b. Therefore, the data could be combined and averaged for larger group analysis. The chronic progressive group had higher myelin basic protein-like material/creatinine ratios (p=0.0349) than the relapsing-remitting group, but there were no differences between chronic progressive and relapsing-remitting groups in values of creatinine or myelin basic protein-like material (data not shown). When the amount of myelin basic protein-like material excreted over 24 hours was analyzed, there was no significant difference (p=0.1775). The trend is in the direction of the chronic progressive having a higher value than the relapsing-remitting group.

EXAMPLE 15
Effect of IFNβ-1b Treatment on Urinary MBPLM

For Group 1 there were trends for differences among the three treatment groups. Overall and at each visit, the high dose IFNβ-1b group had higher values of urinary myelin basic protein-like material than both placebo and low dose IFNβ-1b groups. However, these group differences at the start of the trial approached but did not reach a significant level (p=0.0753). Although not statistically significant, these trends implied that in the randomization of patients to the three treatment groups at the outset of the trial there had been an inadvertent selection of multiple sclerosis patients with higher urinary myelin basic protein-like material values in the high-dose treatment group. For visit two, the difference reached a significant level overall (p=0.0365) with the urinary myelin basic protein-like material elevated in the high dose compared to the placebo (p=0.0204) and high dose compared to the low dose treatment (p=0.0296) groups. This indicated that the differences in urinary myelin basic protein-like material values noted in the three treatment groups at the beginning of the trial became more evident by the beginning of the second year of the trial. This difference became insignificant again by the third visit because of an increase of urinary myelin basic protein-like material in the placebo group between visits one and three (p=0.0056) and between visits two and three (p=0.0014). Because of the significant differences in urinary myelin basic protein-like material values among the randomly assigned treatment groups, correlation studies for treatment effects were precluded for Group 1. Specifically, there was no definite treatment effect demonstrable on the basis of the urine levels of myelin basic protein-like material.

Group 3 patients, from whom urine was collected in mid-trial, were also analyzed for treatment effect, and creatinine values were not different among the placebo, low dose IFNβ-1b or high dose IFNβ-1b groups (data not shown). However, the value for myelin basic protein-like material (ng/ml) was significantly higher in the placebo group than in either the low dose (p=0.0005) or the high dose (p=0.0023) IFNβ-1b groups. Similarly, the values for myelin basic protein-like material/creatinine were significantly higher in the placebo group than in either the low dose (p=0.0003) or high dose (p=0.0014) IFNβ-1b groups. These differences between placebo and low dose (p=0.0001) and placebo and high dose (p=0.0039) groups were also evident when the myelin basic protein-like material measurements were expressed as total amount during a 24-hour period. Since there were no baseline samples collected for Group 3, these significant differences, as striking as they are, possibly could have arisen from the random assignment to treatment groups.

In a two-factor ANOVA, the treatment and progression variables were studied simultaneously in Group 3. A significant interaction existed between effect on the value of myelin basic protein-like material expressed as a 24-hour collection (p=0.0108) or adjusted for creatinine (p=0.0303). When analyzed further, it was clearly demonstrated that the relapsing-remitting group receiving placebo and which became chronic progressive was the major variable accounting for these differences. By the same analytic method, there was no significant interaction of these same two variables on the values of creatinine or myelin basic protein-like material (ng/ml). Covariance analyses, performed to account for the effect of the variation in length of time in the clinical trial when the specimens were collected, gave the same results as the ANOVA's. The simpler ANOVA results are therefore presented. It was noted that the standard deviations for these measures in Group 3 were large and proportional to the means. Since the arithmetic means departed from a normal distribution, a logarithmic transformation was applied and the data reanalyzed. The myelin basic protein-like material variable measured over a 24-hour period remained significant (p=0.0283), while the myelin basic protein-like material adjusted for creatinine no longer had a significant interaction between the treatment and progression variables (p=0.0792).

In another effort to delineate the timing and prediction of a relapsing-remitting and chronic progressive course and any treatment effect, all urine data from Groups 1 and 2 were combined. In so doing it was first shown that patients in the chronic progressive and relapsing-remitting categories were equally distributed among the three treatment groups (p=0.901). When grouped by any treatment versus placebo comparison, there was not a significant (p=0.891) treatment effect. The means and slopes of urinary myelin basic protein-like material were computed for all patients. The only significant difference was found in the average level of myelin basic protein-like material (ng/ml) with respect to progression (p=0.0051). There was no significant effect in regard to treatment. In another attempt to detect predictive differences in urinary myelin basic protein-like material values for the relapsing-remitting and chronic progressive groups, means and slopes for relapsing-remitting and chronic progressive groups were computed using values obtained before the transition to chronic progressive from relapsing-remitting. There was a significant difference between the relapsing-remitting and chronic progressive groups in average myelin basic protein-like material (ng/ml) (p=0.0169) and average creatinine (mg/ml) (p=0.0378) before transition. A higher slope in the level of myelin basic protein-like material/creatinine (ng/mg) correlated with a change of relapsing-remitting to chronic progressive course (p=0.0052). There were no significant differences according to treatment.

EXAMPLE 16

Repeat Analysis with Urinary myelin basic protein-like material Measured with Reagents R3794 and F41

Three antibody reagents are now available which detect urinary myelin basic protein-like material. These are R110 (22), which has been used to obtain the myelin basic protein-like material values analyzed above, polyclonal reagent R3794 and mAb F41 (35). All three react with cryptic epitopes in myelin basic protein (22, 35). The urine samples collected annually (Group 1) were tested in RIAs with F41 and R3794, and the values obtained were compared with those from the measurements with R110. R110 and R3794, which recognize epitopes in myelin basic protein peptide 83–89 or 84–89, respectively, revealed similar correlations for Group 1. Monoclonal antibody F41, which recognizes a different epitope in myelin basic protein peptide 80–85, demonstrated no difference.

EXAMPLE 17

The present invention demonstrates that the level of urine myelin basic protein-like material can be utilized successfully as a marker of disease status in adults with multiple sclerosis. Myelin basic protein-like material increases in patients changing from a relapsing-remitting to a progressive course, possibly reflecting attempted or failed remyelination. Scant information exists concerning the presence of or specific levels of urine myelin basic protein-like material during infancy and childhood when myelination is most active. If urine myelin basic protein-like material exhibits a developmental profile corresponding to that of forebrain myelination, certain inferences should follow deviations from normal. Myelin basic protein-like material, as shown herein, can serve as a monitor of neurodevelopmental status in infants at risk for adverse outcomes.

The present invention demonstrates the pattern of myelin basic protein-like material in normal children ranging in age from birth at term to age 15 years. Myelin basic protein-like material was assayed in urine from 242 infants and children as described above. Myelin basic protein-like material was detectable in urine from newborns although at substantially lower levels than in adults (87.2±38.5 ng/mg creatinine). Whether expressed as ng/ml urine or ng/mg creatinine, myelin basic protein-like material levels were low from birth though 12 months, then increased linearly through age 5 exceeding established control values for adults by more than 2-fold. Thereafter, myelin basic protein-like material levels decline to adult levels by age 8. Human urine myelin basic protein-like material exhibits a developmental profile that parallels the onset of normal myelination actually exceeding normal values through early childhood. Thus, urine myelin basic protein-like material can serve as a useful marker for normal or aberrant myelination in the developing child.

The present invention demonstrates that the level of urinary myelin basic protein-like material correlates with or is a predictor of the transition of phases of multiple sclerosis from relapsing-remitting to chronic progressive. The elevated level of urinary myelin basic protein-like material occurred well in advance of the clinical designation of a chronic progressive course, indicating that the level of urinary myelin basic protein-like material may be important in stratifying multiple sclerosis patients prior to entry to a clinical trial. The exact level of urinary myelin basic protein-like material which signals a progressive course must be examined closely because of the fluctuations in level over time in the same patient.

Because the conditions and timing of collection of urine specimens were introduced into a clinical trial not specifically designed to address a change in urinary myelin basic protein-like material levels, the results revealed the imperfections on how the urine was sampled and the myelin basic protein-like material measurements were made. The greatest challenge to the use of urinary myelin basic protein-like material as a surrogate marker is the confounding effect of urinary levels of creatinine. For reasons that are currently unclear, patients with chronic progressive-multiple sclerosis also had higher levels of creatinine. Such a change in creatinine concordant with that of myelin basic protein-like material abolished the predictive use in Group 1 of myelin basic protein-like material/creatinine, the measure shown previously to be the most desirable (22, 23) to normalize for glomerular function. The effect of creatinine was most noted in Group 2, which had a much larger number. It was in Group 2 that the level of myelin basic protein-like material alone or myelin basic protein-like material/creatinine was significantly higher in the chronic progressive cases. Furthermore, the slope of rise in myelin basic protein-like material/creatinine in Group 2 and the 24-hour collections in Group 3 also showed a correlation of urinary myelin basic protein-like material and chronic progressive course. The IFNβ-1b trial was completed before it became clear that urinary myelin basic protein-like material was not directly correlated with acute clinical disease activity (23) as is CSF myelin basic protein-like material (19, 36). Specifically, levels of urinary myelin basic protein-like material/creatinine do not correlate with clinical relapse, gadolinium enhancement of lesions detected on cranial MRI or level of myelin basic protein-like material in CSF (23). In the present invention, urinary myelin basic protein-like material did not correlate with the number of clinical relapses. Urinary myelin basic protein-like material levels did correlate overall with the number of lesions and total lesion burden determined by T2-weighted cranial MRI.

Since a beneficial effect of IFNβ-1b was demonstrated in the clinical trial (24), a correlation or prediction of treatment effect was sought. The level of urinary myelin basic protein-like material rose more in the placebo group than in either of the IFNβ-1b treatment groups, and in Group 3 it was clearly the placebo-treated patients with a transition to the chronic progressive phase who had the highest levels of urinary myelin basic protein-like material. However, the trial, in which patients were randomly assigned to placebo, low-dose IFNβ-1b or high-dose IFNβ-1b did not control for urinary myelin basic protein-like material on entry.

The mechanism for a rise in the level of urinary myelin basic protein-like material is not yet known. The information available indicates that large myelin basic protein peptides are likely to be rapidly cleared (37) and degraded (38) in the kidney. Since the immunochemical form of myelin basic protein-like material in the urine is different from that in the CSF (22) and since the levels of myelin basic protein-like material in CSF and urine are not directly related (23), the mechanism, presumed to be acute myelin or oligodendrocyte damage, for the rise of myelin basic protein-like material in CSF, is unlikely to be the same for that in the urine. Axonal contact upregulates the synthesis of myelin basic protein synthesis by oligodendrocytes in the absence of axons (39). Thus oligodendrocytes in the demyelinated and chronic lesions of multiple sclerosis may be able to continue to synthesize myelin basic protein in the chronic progressive course of multiple sclerosis when axonal loss is presumed to occur. Synthesized myelin basic protein which is not incorporated into myelin precursors or myelin itself may reach the circulation and be cleared and degraded by the kidney. The small, cryptic epitope of myelin basic protein would enter urine and be detectable in the immunoassay.

The present invention represents the first approximation of the correlation and prediction of the level of myelin basic protein-like material in urine and other body fluids and the future disease course of multiple sclerosis. Even though the specific chemical nature of urinary myelin basic protein-like material remains to be determined, the immunochemical detection of it as a cryptic epitope in the carboxyl portion of myelin basic protein peptide 80–89 in previous studies (40) and the replication of the measurements reported with a second antibody with a nearly identical epitope recognition (35), add to the validity of the immunoassay. The relationship of urinary myelin basic protein-like material with chronic progressive disease, more precise classification of disability status, clarification of the differences of the sub-types of multiple sclerosis, especially relapsing-progressive and relapsing-remitting, and the delineation of the type of cranial MRI technique to be utilized makes the outcomes of future clinical trials in multiple sclerosis more accurate and their conduct more rapid.

The following references were cited herein:
1. Anderson et al., Ann Neurol 1992;31:333–336
2. Weinshenker et al., Neurologic Clinics 1995;13:119–146
3. Weinshenker et al., Brain 1989;112:1419–1428
4. Runmarker et al., Brain 1993;116:117–134
5. Paty et al., In: Rudick R A, Goodkin D E, eds. Treatment of Multiple Sclerosis: Trial Design Results and Future Perspectives. London: Springer-Verlag, 1992:47–90
6. Rodriguez et al., Neurology 1994;44:28–33
7. Goodkin et al., Arch Neurol 1989;46:1107–1112
8. Weinshenker et al., Can J Neurol Sci 1987;14:255–261
9. Runmarker et al., J Neurol 1994;241:385–390
10. Sharief et al., N Engl J Med 1991;325:467–472
11. Noseworthy et al., Neurology 1993;43:A355
12. Paty et al., Neurology 1993;43:662–667
13. Filippi et al., Neurology 1994;44:635–641
14. Franket al., Ann Neurol 1994;36(Suppl):S86–S90
15. Thompson et al., Br Med J 1990;300:631–634
16. Gass et al., Ann Neurol 1994;36:62–67
17. Morell et al., In: Siegel et al., eds. Basic Neurochemistry. 4th ed. NY: Raven Press, 1994:117–143
18. Cohen et al., N Engl J Med 1976;295:1455–1457
19. Whitaker J N, Neurology 1977;27:911–920
20. Whitakeret al., Ann Neurol 1993;33:10–17
21. Whitaker et al., Ann Neurol 1993;34:273
22. Whitaker et al., Ann Neurol 1987;22:648–655
23. Whitaker et al., Ann Neurol 1994;35:577–585
24. The IFNb Multiple Sclerosis Study Group. Neurology 1993;43:655–661
25. Kurtzke J F. Neurology 1983;33:1444–1452
26. Sipe et al., Neurology 1984;34:1368–1372
27. Reder et al., J Interferon Res 1992;12:195–198
28. Ostle, M., Statistics in Research. 4th ed. Ames: The Iowa State University Press, 1988
29. Snedecor G W, Cochran W G. Statistical Methods. 7th ed. Ames: The Iowa State University Press, 1980
30. Draper N R, Smith H. Applied Regression Analysis. 2nd ed. New York: John Wiley & Sons, 1966
31. Daniel WW. Applied Nonparametric Statistics. Boston: Houghton Mifflin, 1978
32. Prentice R L. Linear Rank Tests with Right Censored Data. Biometrika 1978;65:167–179
33. Cox D R. Regression models and life-tables. J Roy Statist Soc, Series B 1972;34:187–220
34. Montgomery D C. Design and analysis of experiments. 2nd ed. New York: John Wiley & Sons, 1984:192–214
35. Whitaker et al., J Neuroimmunol 1994;52:53–60
36. Whitaker et al., Ann Neurol 1980;7:58–64
37. Bashir et al., Neurology 1980;30:1184–1192
38. Whitaker et al., Neurology 1983;33:744–749
39. Mirsky et al., J Cell Biol 1980;84:483–494
40. Whitaker et al., J Neurochem 1990;55:568–576
41. Whitaker et al., Multiple Sclerosis 1995; In Press Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of predicting an increase in the amount of lesions and total lesion area of a multiple sclerosis patient, comprising the steps of:
   a) measuring myelin basic protein-like material in multiple urine samples from said patient over time; and
   b) comparing the amount of said myelin basic protein-like material in each urine sample from said patient to an art-accepted standard; wherein an increase in said urinary myelin basic protein-like material in said multiple urine samples is predictive of said increase in the amount of lesions and total lesion area in said multiple sclerosis patient.

2. The method of claim 1, wherein said measuring of urinary myelin basic protein-like material is by a radioimmunoassay.

3. The method of claim 2, wherein said radioimmunoassay is a double-antibody radioimmunoassay.

4. The method of claim 3, wherein said double-antibody radioimmunoassay uses rabbit antiserum directed towards an immunogen, wherein said immunogen comprises a 30:70 mixture of bovine myelin basic protein residues 45–89 and bovine myelin basic protein residues 43–88, wherein the antisera recognizes a cryptic epitope in myelin basic protein consisting essentially of myelin basic protein residues 80–89, wherein said antisera is specific for myelin basic protein-like material and does not cross-react with myelin basic protein, radioiodinated bovine myelin basic protein residues 45–89, or fragments thereof, as a radioligand, bovine myelin basic protein residues 83–89 as a radioimmunoassay standard and goat anti-rabbit IgG as a second antibody.

5. The method of claim 1, wherein said art-accepted standard for said comparison is selected from the group consisting of urinary creatinine levels, random urinary volume per defined period of collection time for each said urine sample and total urinary volume per defined period of collection time for each said urine sample.

6. The method of claim 5, wherein said defined period of collection time for each said urine sample is 24 hours.

7. A method of predicting normal age-related changes in myelination in a developing child, comprising the steps of:
   a) measuring myelin basic protein-like material in multiple urine samples from said child over time; and
   b) comparing the amount of said myelin basic protein-like material in each urine sample from said child to an art-accepted standard; wherein lower levels of urinary myelin basic protein-like material are present from birth through approximately one year of age relative to established values for adults, wherein levels of urinary myelin basic protein-like material in said multiple urine samples increase linearly from approximately one year of age through approximately five years of age of said child exceeding said established values for adults, wherein levels of urinary myelin basic protein-like material in said multiple urine samples decrease between approximately five years of age and approximately eight years of age of said child to approximate established values for adults, wherein said levels of urinary myelin basic protein-like material in said multiple urine samples are predictive of normal age-related changes in myelination in said developing child.

8. The method of claim 7, wherein said measuring of said urinary myelin basic protein-like material is by a radioimmunoassay.

9. The method of claim 8, wherein said radioimmunoassay is a double-antibody radioimmunoassay, wherein said double-antibody radioimmunoassay uses rabbit antiserum directed towards an immunogen, wherein said immunogen comprises a 30:70 mixture of bovine myelin basic protein residues 45–89 and bovine myelin basic protein residues 43–88, wherein the antisera recognizes a cryptic epitope in myelin basic protein consisting essentially of myelin basic protein residues 80–89, wherein said antisera is specific for myelin basic protein-like material and does not cross-react with myelin basic protein, radioiodinated bovine myelin basic protein residues 45–89, or fragments thereof, as a radioligand, bovine myelin basic protein residues 83–89 as a radioimmunoassay standard and goat, anti-rabbit IgG as a second antibody.

10. The method of claim 7, wherein said art-accepted standard for said comparison is selected from the group consisting of urinary creatinine levels, random urinary volume per defined period of collection time for each said urine sample and total urinary volume per defined period of collection time for each said urine sample.

11. The method of claim 10, wherein said defined period of collection time for each said urine sample is 24 hours.

* * * * *

UNITED STATES PATENT AND TRADEMARK OFFICE
CERTIFICATE OF CORRECTION

PATENT NO.    : 5,998,150
DATED         : December 7, 1999
INVENTOR(S)   : Whitaker et al.

It is certified that error appears in the above-identified patent and that said Letters Patent is hereby corrected as shown below:

Column 1,
Line 11, please insert the following paragraph before "Background of the Invention":

-- FEDERAL FUNDING
    This invention was produced in part using funds obtained through grant number NS23240 from the National Institutes of Health. Consequently, the federal government has certain rights in this invention. --

Signed and Sealed this

Twenty-seventh Day of August, 2002

Attest:

Attesting Officer

JAMES E. ROGAN
Director of the United States Patent and Trademark Office